US012332225B2

(12) United States Patent
Dwyer et al.

(10) Patent No.: US 12,332,225 B2
(45) Date of Patent: Jun. 17, 2025

(54) METHOD FOR DETERMINING SMALL MOLECULE COMPONENTS OF A COMPLEX MIXTURE, AND ASSOCIATED APPARATUS AND COMPUTER PROGRAM PRODUCT

(71) Applicant: METABOLON, INC., Morrisville, NC (US)

(72) Inventors: Rex Allen Dwyer, Raleigh, NC (US); Elizaveta Freinkman, Cary, NC (US); Anne M. Evans, Cary, NC (US)

(73) Assignee: METABOLON, INC., Morrisville, NC (US)

( * ) Notice: Subject to any disclaimer, the term of this patent is extended or adjusted under 35 U.S.C. 154(b) by 254 days.

(21) Appl. No.: 18/041,034

(22) PCT Filed: Aug. 13, 2021

(86) PCT No.: PCT/IB2021/057493
§ 371 (c)(1),
(2) Date: Feb. 8, 2023

(87) PCT Pub. No.: WO2022/034552
PCT Pub. Date: Feb. 17, 2022

(65) Prior Publication Data
US 2023/0288384 A1    Sep. 14, 2023

Related U.S. Application Data

(60) Provisional application No. 63/116,239, filed on Nov. 20, 2020, provisional application No. 63/065,761, filed on Aug. 14, 2020.

(51) Int. Cl.
*G01N 30/86* (2006.01)
*G01N 30/72* (2006.01)
*G01N 30/88* (2006.01)

(52) U.S. Cl.
CPC ......... *G01N 30/86* (2013.01); *G01N 30/7233* (2013.01); *G01N 2030/8648* (2013.01); *G01N 2030/8813* (2013.01)

(58) Field of Classification Search
CPC ............... G01N 30/86; G01N 30/7233; G01N 2030/8648; G01N 2030/8813; H01J 49/0036; H01J 49/0045; G16C 20/20
See application file for complete search history.

(56) References Cited

U.S. PATENT DOCUMENTS

| 7,197,401 B2* | 3/2007 | Hastings | H01J 49/0036 |
| | | | 702/30 |
| 2004/0041089 A1* | 3/2004 | Zhu | H01J 49/0036 |
| | | | 250/282 |

(Continued)

FOREIGN PATENT DOCUMENTS

| GB | 2574269 A | 12/2019 |
| JP | 2008-170260 | 7/2008 |

(Continued)

OTHER PUBLICATIONS

Simón-Manso Yamil et al, "Mass Spectrometry Fingerprints of Small-Molecule Metabolites in Biofluids: Building a Spectral Library of Recurrent Spectra for Urine Analysis", *Analytical Chemistry*, Aug. 19, 2019, vol. 91(18), pp. 12021-12029.

(Continued)

*Primary Examiner* — David J Bolduc
(74) *Attorney, Agent, or Firm* — Womble Bond Dickinson (US) LLP

(57) ABSTRACT

A data analysis method for a component separation/tandem mass spectrometer system, including first and second MS steps which data therefrom includes respective sample components (MS1-SC, MS2-SC), includes analyzing per sample a data set for MS2-SC to determine mass-to-charge ratio and retention index (m/z-RI) for each MS2-SC. m/z-RI for each (Continued)

Figure 1:
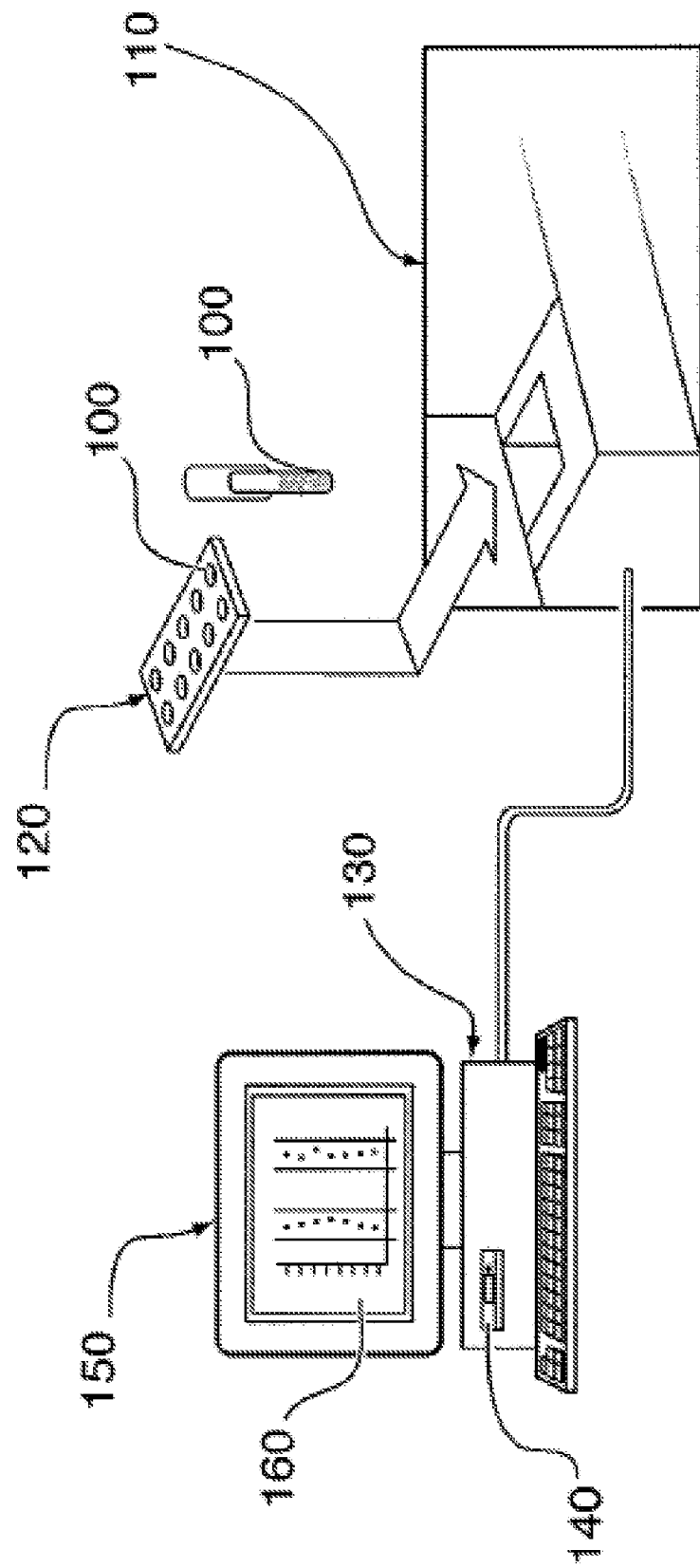

MS2-SC is compared to a known compound library and matching MS2-SC removed from the data set, the remaining MS2-SC being candidate MS2-SC. Clusters are formed across the candidate MS2-SC, each having m/z-RI within respective ranges per cluster. For each sample within each cluster, MS1-SC within the cluster ranges are retrieved. For each cluster, at most one consensus MS1-SC represents each sample, with corresponding consensus MS2-SC and m/z-RI, and designated as a molecular ion or derivative thereof. Clusters are grouped by consensus RI and candidate clusters from each group are selected and correlated by consensus parameters with an unknown compound.

54 Claims, 5 Drawing Sheets

(56) References Cited

U.S. PATENT DOCUMENTS

| | | | | |
|---|---|---|---|---|
| 2005/0065733 | A1* | 3/2005 | Caron | G16C 20/80 702/22 |
| 2005/0261838 | A1* | 11/2005 | Andreev | H01J 49/004 702/22 |
| 2006/0172365 | A1* | 8/2006 | May | G01N 33/6848 435/23 |
| 2008/0121793 | A1* | 5/2008 | Yamaguchi | H01J 49/0081 250/282 |
| 2009/0026360 | A1* | 1/2009 | Yamauchi | H01J 49/0036 250/281 |
| 2010/0239139 | A1* | 9/2010 | Hunt | G06F 18/23 382/128 |
| 2011/0125416 | A1* | 5/2011 | Noda | H01J 49/0036 702/30 |
| 2013/0060477 | A1* | 3/2013 | Sen Gupta | G16C 20/20 702/19 |
| 2014/0088885 | A1* | 3/2014 | Lee | G01N 30/96 702/25 |
| 2016/0313334 | A1* | 10/2016 | Zaidi | C12Q 1/6886 |
| 2017/0358434 | A1* | 12/2017 | Matsuura | G16C 20/70 |
| 2018/0166265 | A1* | 6/2018 | Geromanos | H01J 49/0031 |
| 2019/0317047 | A1* | 10/2019 | Astarita | G01N 27/623 |
| 2020/0224144 | A1* | 7/2020 | Love | C12M 41/44 |
| 2021/0208117 | A1* | 7/2021 | Murase | G01N 30/86 |

FOREIGN PATENT DOCUMENTS

| | | |
|---|---|---|
| WO | WO 2015/054468 | 4/2015 |
| WO | WO 2015/184048 | 12/2015 |
| WO | WO 2019/229723 | 12/2019 |

OTHER PUBLICATIONS

Du Xiuxia et al, "A preparatory study of how to construct consensus mass spectra of recurrent unknown metabolites from untargeted GC-MS metabolomics data", *International Journal of Mass Spectrometry*, vol. 427, Nov. 9, 2017, pp. 73-78.

Tsugawa Hiroshi Ed—Jin Yong-Su et al., "Advances in computational metabolomics and databases deepen the understanding of metabolisms", *Current Opinion in Biotechnology*, London, GB, vol. 54, Feb. 6, 2018, pp. 10-17.

Yi Lunzhao et al, "Chemometric methods in data processing of mass spectrometry-based metabolomics: A review", *Analytica Chimica Acta*, Elsevier, Amsterdam, NL, vol. 914, Feb. 16, 2016, pp. 17-34.

Sindelar Miriam et al, "Chemical Discovery in the Era of Metabolomics", *Journal of the American Chemical Society*, vol. 142(20), Apr. 10, 2020, pp. 9097-9105.

* cited by examiner

METHOD FOR DETERMINING SMALL MOLECULE COMPONENTS OF A COMPLEX MIXTURE, AND ASSOCIATED APPARATUS AND COMPUTER PROGRAM PRODUCT

CROSS-REFERENCE TO RELATED APPLICATIONS

This application is a national stage filing under 35 U.S.C. 371 of PCT/IB2021/057493, filed Aug. 13, 2021, which International Application was published by the International Bureau in English on Feb. 17, 2022, as WO 2022/034552, and application claims priority from U.S. Application No. 63/065,761, filed on Aug. 14, 2020, and U.S. Application No. 63/116,239, filed on Nov. 20, 2020, which applications are hereby incorporated in their entirety by reference in this application.

BACKGROUND

Field of the Disclosure

Aspects of the present disclosure relate to the analysis and determination of small molecule components of a complex mixture and, more particularly, to a method and associated apparatus and computer program product for analyzing and discerning small molecule components or compounds of a complex mixture, with such small molecule analysis including metabolomics, which is the study of small molecules produced by an organism's metabolic processes, or other analysis of small molecules produced through metabolism.

Description of Related Art

Small molecules or compounds are extremely diverse and numerous. The total number of compounds found in nature is unknown, but it is generally estimated to be at least in the tens of thousands. Particular compound data repositories (libraries or databases) can contain approximately 5,000 named and 2,000 unnamed compounds; therefore, thousands of potentially significant unnamed compounds are not yet being reported and cataloged. Discoverable unnamed compounds are detectable by existing chromatography/mass spectrometry methods in a discovery process, but such unnamed compounds are not currently reported because they do not match any existing known compound in a database or library.

To present, discovery of unnamed compounds has generally been performed with the assistance of a graphical interactive tool. However, while such a graphical interactive tool provides indispensable assistance to the scientist, it is not fully automated, is very time-consuming, discovers many false positives and has other technical limitations. As a result, it is infrequently used, and, as a consequence, the number of unnamed compounds reported in a sample remains stagnant. There is little motivation to add unnamed compounds to a database or library if their structures and identity will not be subsequently determined.

Chromatography/mass spectrometry methods have the ability to generate data leading to the detection and identification of individual compounds in a sample. One way to accurately identify compounds detected in a sample is by using a library or database of authentic chemical standards. However, in many contexts it is desirable to discover novel unnamed compounds that are not yet part of such a library or database. The challenge in identifying novel unnamed compounds using data derived using mass spectrometric methods is that novel unnamed compounds are detected as ion features or features (as defined by a characteristic mass-to-charge ratio and retention index). In a typical sample there is a large number of features detected, most of which do not correspond to unique compounds, but are rather redundant representations of other known compounds. Therefore, processing and characterizing the features in a way that provides enrichment for true novel unnamed compounds can be time consuming and error-prone.

In addition to identifying recurring unnamed compounds without human input, it would be desirable for a methodology to provide additional information regarding the unnamed compound to help the scientist prioritize unnamed compounds. In addition, it would be desirable for the methodology to remove/filter out feature data from the analysis related to existing known compounds present in a library or database as well as other irrelevant features such as background compound contaminants, and chromatographic artifacts. It would also be desirable for the methodology to analyze the remaining features and to output candidate compounds with consensus m/z, retention index (e.g., the retention time of a feature/compound normalized to the retention times of adjacently eluting known ions/compounds), isotopic signatures, consensus MS/MS spectra, and peak areas for optional statistical analysis.

SUMMARY

The above and other needs are met by aspects of the present disclosure which, in some aspects, provides a fully automated method, apparatus, and computer program product for detecting new biochemicals in one or more samples in an automated manner that is faster and more accurate than existing methods. For example, a small study can be analyzed in an hour or less, and a study of 6200 samples was analyzed in about 8 hours using a commodity desktop computer. In contrast, current commercially available software for performing similar functions of identifying biochemicals in samples, is estimated to require 4-5 hours to analyze a set of 60 samples, while performing substantially fewer functions. Aspects of the disclosure also remove noise and other irrelevant features more effectively, and optionally can remove features that have no statistical significance to the study.

In some aspects, the methodology relies primarily on MS scans rather than integrated peaks, which makes it much faster and likely more accurate than other prior art methods. The methodology further discards features corresponding to any known features associated with any existing library entry (including in-source fragments, adducts, and dimers), and also discards features that have no plausible molecular formula. Aspects of the present disclosure efficiently analyze about 1500 possible adductive and isotopic relationships among ions in MS scans. Analysis of this large number of mass relationships can be achieved by using software to solve mathematical equations symbolically in a free-standing program that itself writes part of the program code. The methodology of the present disclosure is applicable to a single sample, or is applicable across a plurality of samples. The methodology of the present disclosure may also optionally discard features that have no statistical significance with respect to the metadata of the study under consideration.

One particular aspect of the present disclosure provides a method of analyzing data for one or more samples, with the data for each sample being obtained from a component separation and tandem mass spectrometer system comprising a separation portion, including a liquid chromatograph, a gas chromatograph, a supercritical fluid chromatograph, or a capillary electrophoresis analyzer, and a first mass spectrometry step or provision (MS1) and a second mass spectrometry step or provision (MS2). The data from the MS1 includes MS1 sample components and the data from the MS2 includes MS2 sample components. Such a method comprises analyzing, for each sample, a data set for a plurality of MS2 sample components to determine a precursor ion mass-to-charge ratio (m/z) and a retention index (RI) for each MS2 sample component. The precursor ion m/z and the RI for each MS2 sample component is compared to precursor ion mass-to-charge ratios and retention indices of known compounds, and any MS2 sample component corresponding to one of the known compounds removed from the data set. Remaining MS2 sample components in the data set are candidate MS2 sample components. Component clusters are formed across the candidate MS2 sample components, with each component cluster including candidate MS2 sample components each having the precursor ion m/z and the RI within respective ranges for the component cluster. For each sample within each component cluster, one or more MS1 sample components within the respective precursor ion m/z and RI ranges for the component cluster is retrieved. For each component cluster, at most one consensus MS1 sample component is determined by aggregating the one or more MS1 sample components within the respective precursor ion m/z and RI ranges, and the consensus MS1 sample component represents each sample. The consensus MS1 sample component is associated with a corresponding consensus MS2 sample component, consensus precursor ion m/z, and consensus RI determined by aggregating the MS2 sample components and associated precursor ion m/z and the RI within the component cluster. For each component cluster, it is determined whether the consensus MS1 sample component indicates a molecular ion or a derivative relationship to the molecular ion. Component clusters are grouped according to consensus RI, and one or more component clusters selected from each group of component clusters, with the one or more component clusters being candidate component clusters. The consensus precursor ion m/z, the consensus RI, the consensus MS1 sample component, and the consensus MS2 sample component of the candidate component clusters are then correlated with an unknown compound in the samples.

The present disclosure thus includes, without limitation, the following example embodiments:

Example Embodiment 1: A method of analyzing data for one or more samples, the data for each sample being obtained from a component separation and tandem mass spectrometer system comprising a separation portion, including a liquid chromatograph, a gas chromatograph, a supercritical fluid chromatograph, or a capillary electrophoresis analyzer, and a first mass spectrometry step or provision (MS1) and a second mass spectrometry step or provision (MS2), wherein the data from the MS1 includes MS1 sample components and the data from the MS2 includes MS2 sample components, said method comprising analyzing, for each sample, a data set for a plurality of MS2 sample components to determine a precursor ion mass-to-charge ratio (m/z) and a retention index (RI) for each MS2 sample component; comparing the precursor ion m/z and the RI for each MS2 sample component to precursor ion mass-to-charge ratios and retention indices of known compounds and removing any MS2 sample component from the data set corresponding to one of the known compounds, with remaining MS2 sample components in the data set being candidate MS2 sample components; forming component clusters across the candidate MS2 sample components, each component cluster including candidate MS2 sample components each having the precursor ion m/z and the RI within respective ranges for the component cluster; for each sample within each component cluster, retrieving one or more MS1 sample components within the respective precursor ion m/z and RI ranges for the component cluster; for each component cluster, determining at most one consensus MS1 sample component, by aggregating the one or more MS1 sample components within the respective precursor ion m/z and RI ranges, to represent each sample, and associating the consensus MS1 sample component with a corresponding consensus MS2 sample component, consensus precursor ion m/z, and consensus RI determined by aggregating the MS2 sample components and associated precursor ion m/z and the RI within the component cluster; for each component cluster, determining whether the consensus MS1 sample component indicates a molecular ion or a derivative relationship to the molecular ion; grouping component clusters according to consensus RI and selecting one or more component clusters from each group of component clusters, the one or more component clusters being candidate component clusters; and correlating the consensus precursor ion m/z, the consensus RI, the consensus MS1 sample component, and the consensus MS2 sample component of the candidate component clusters with an unknown compound in the samples.

Example Embodiment 2: The method of any preceding example embodiment, or combinations thereof, wherein removing any MS2 sample component from the data set corresponding to one of the known compounds comprises removing any of a known molecular ion, a background artifact, a chromatographic artifact, or a derivative relationship of the known molecular ion, a mass relationship of the known molecular ion, the background artifact, or the chromatographic artifact, corresponding to one of the known compounds, from the data set.

Example Embodiment 3: The method of any preceding example embodiment, or combinations thereof, wherein removing the derivative relationship of the known molecular ion or the mass relationship of the known molecular ion from the data set comprises removing any of an in-source fragment, an adduct, an isotope, a dimer, an oligomer, a multiple charged species, an adduct of an isotope, or an oligomer of an isotope, from the data set.

Example Embodiment 4: The method of any preceding example embodiment, or combinations thereof, comprising determining precursor ion mass-to-charge ratios and retention indices of the known compounds from the MS1 sample components thereof.

Example Embodiment 5: The method of any preceding example embodiment, or combinations thereof, comprising associating any of the precursor ion m/z, the RI, the MS1 sample components, and the MS2 sample components of each known compound with the respective known compound in a database comprising an ion data repository.

Example Embodiment 6: The method of any preceding example embodiment, or combinations thereof, comprising associating the precursor ion m/z, the RI, MS1 sample components, and the MS2 sample components of each candidate component cluster with the unknown compound in a database comprising an ion data repository.

Example Embodiment 7: The method of any preceding example embodiment, or combinations thereof, comprising determining the retention index by normalizing a retention time for each MS2 sample component.

Example Embodiment 8: The method of any preceding example embodiment, or combinations thereof, wherein forming component clusters across the candidate MS2 sample components comprises forming component clusters across the candidate MS2 sample components using divisive clustering or agglomerative clustering.

Example Embodiment 9: The method of any preceding example embodiment, or combinations thereof, comprising sorting the candidate MS2 sample components by precursor ion mass prior to forming the component clusters across the candidate MS2 sample components.

Example Embodiment 10: The method of any preceding example embodiment, or combinations thereof, comprising sorting the component clusters by retention index to generate secondary component clusters.

Example Embodiment 11: The method of any preceding example embodiment, or combinations thereof, wherein the step of forming component clusters across the candidate MS2 sample components is repeated two or more times.

Example Embodiment 12: The method of any preceding example embodiment, or combinations thereof, wherein comparing the consensus MS1 sample component for each component cluster, across the component clusters, is performed across a plurality of the samples.

Example Embodiment 13: The method of any preceding example embodiment, or combinations thereof, comprising removing any component clusters that are present in less than 5% of the plurality of samples.

Example Embodiment 14: The method of any preceding example embodiment, or combinations thereof, comprising analyzing a plurality of possible derivative relationships or possible mass relationships of the MS1 sample components prior to associating the consensus MS1 sample component with a corresponding consensus precursor ion m/z.

Example Embodiment 15: The method of any preceding example embodiment, or combinations thereof, wherein analyzing the plurality of possible derivative relationships or the plurality of possible mass relationships comprises analyzing the plurality of possible derivative relationships or possible mass relationships using symbolic algebra in a single run to generate computer code for analyzing a set of specified derivative relationships or mass relationships.

Example Embodiment 16: The method of any preceding example embodiment, or combinations thereof, comprising removing any component clusters lacking a plausible molecular formula, prior to grouping the component clusters.

Example Embodiment 17: The method of any preceding example embodiment, or combinations thereof, comprising removing any component clusters lacking statistical significance from metadata of the data of the one or more samples being analyzed, prior to grouping the component clusters.

Example Embodiment 18: The method of any preceding example embodiment, or combinations thereof, comprising prioritizing candidate component clusters having statistical significance with respect to metadata of the data of the one or more samples being analyzed as candidate unknown compounds.

Example Embodiment 19: An apparatus for analyzing data for one or more samples, the data for each sample being obtained from a component separation and tandem mass spectrometer system comprising a separation portion, including a liquid chromatograph, a gas chromatograph, a supercritical fluid chromatograph, or a capillary electrophoresis analyzer, and a first mass spectrometry step or provision (MS1) and a second mass spectrometry step or provision (MS2), the apparatus comprising a processor and a memory storing executable instructions that, in response to execution by the processor, cause the apparatus to at least perform the method steps of any preceding example embodiment, or combinations thereof.

Example Embodiment 20: A computer program product for analyzing data for one or more samples, the data for each sample being obtained from a component separation and tandem mass spectrometer system comprising a separation portion, including a liquid chromatograph, a gas chromatograph, a supercritical fluid chromatograph, or a capillary electrophoresis analyzer, and a first mass spectrometry step (MS1) and a second mass spectrometry step (MS2), the computer program product comprising at least one non-transitory computer readable storage medium having computer-readable program code stored thereon, the computer-readable program code comprising program code for performing the method steps of any preceding example embodiment, or combinations thereof.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure, regardless of whether such features or elements are expressly combined or otherwise recited in a specific embodiment description herein. This disclosure is intended to be read holistically such that any separable features or elements of the disclosure, in any of its aspects and embodiments, should be viewed as intended, namely to be combinable, unless the context of the disclosure clearly dictates otherwise.

It will be appreciated that the summary herein is provided merely for purposes of summarizing some example aspects so as to provide a basic understanding of the disclosure. As such, it will be appreciated that the above described example aspects are merely examples and should not be construed to narrow the scope or spirit of the disclosure in any way. It will be appreciated that the scope of the disclosure encompasses many potential aspects, some of which will be further described below, in addition to those herein summarized. Further, other aspects and advantages of such aspects disclosed herein will become apparent from the following detailed description taken in conjunction with the accompanying drawings which illustrate, by way of example, the principles of the described aspects.

BRIEF DESCRIPTION OF THE SEVERAL VIEWS OF THE DRAWING(S)

Figure 2:
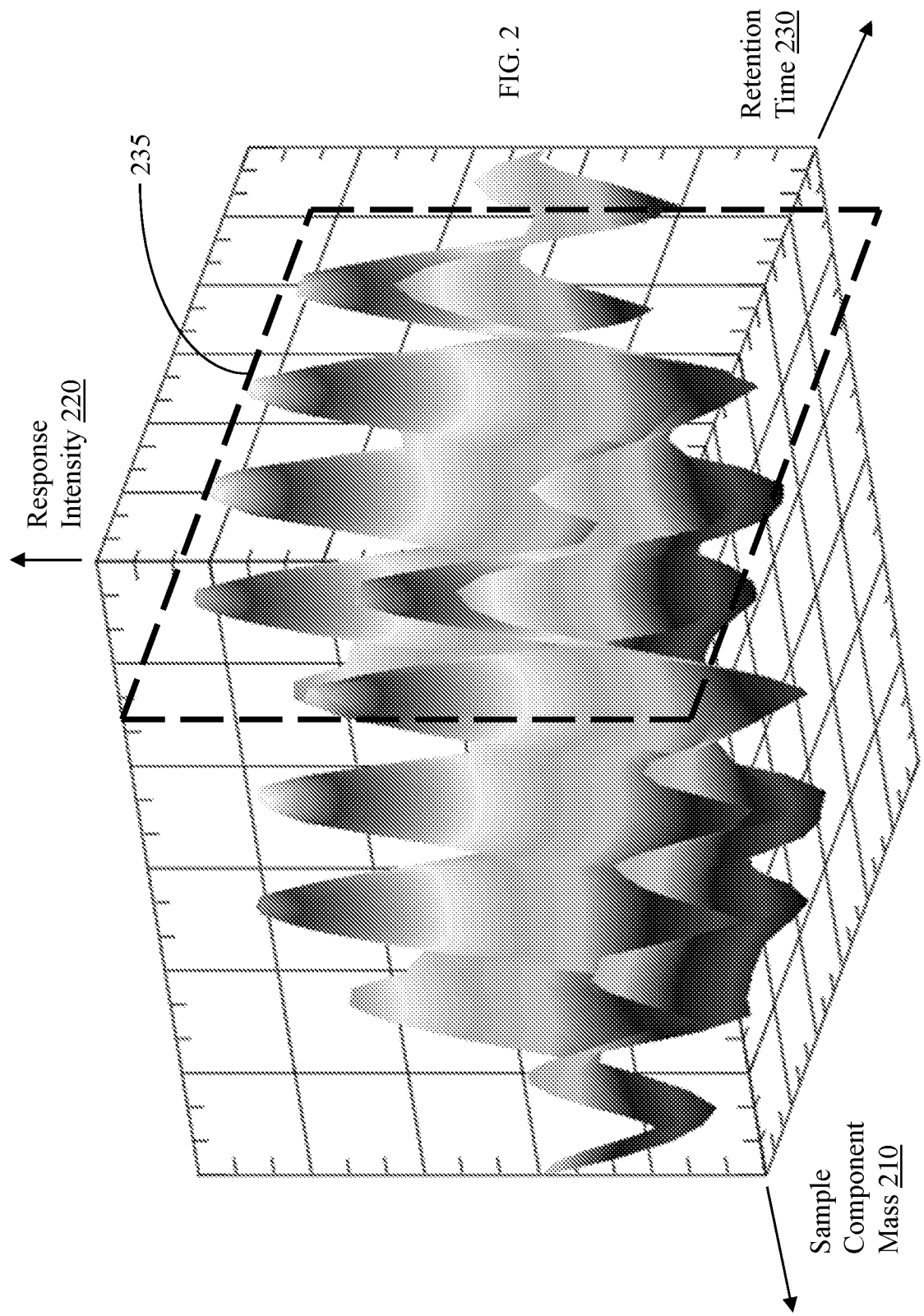
Figure 3:
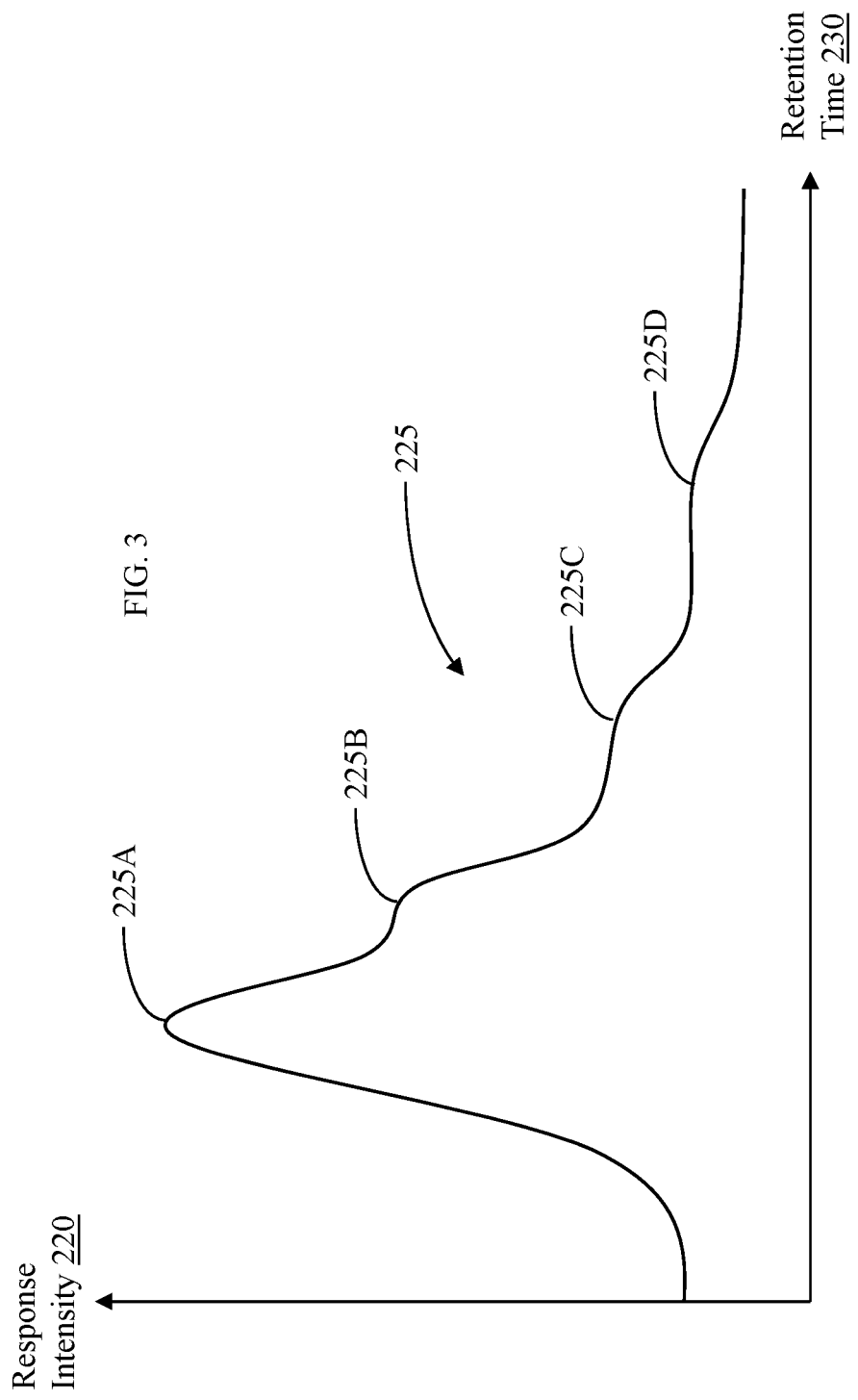
Figure 4:
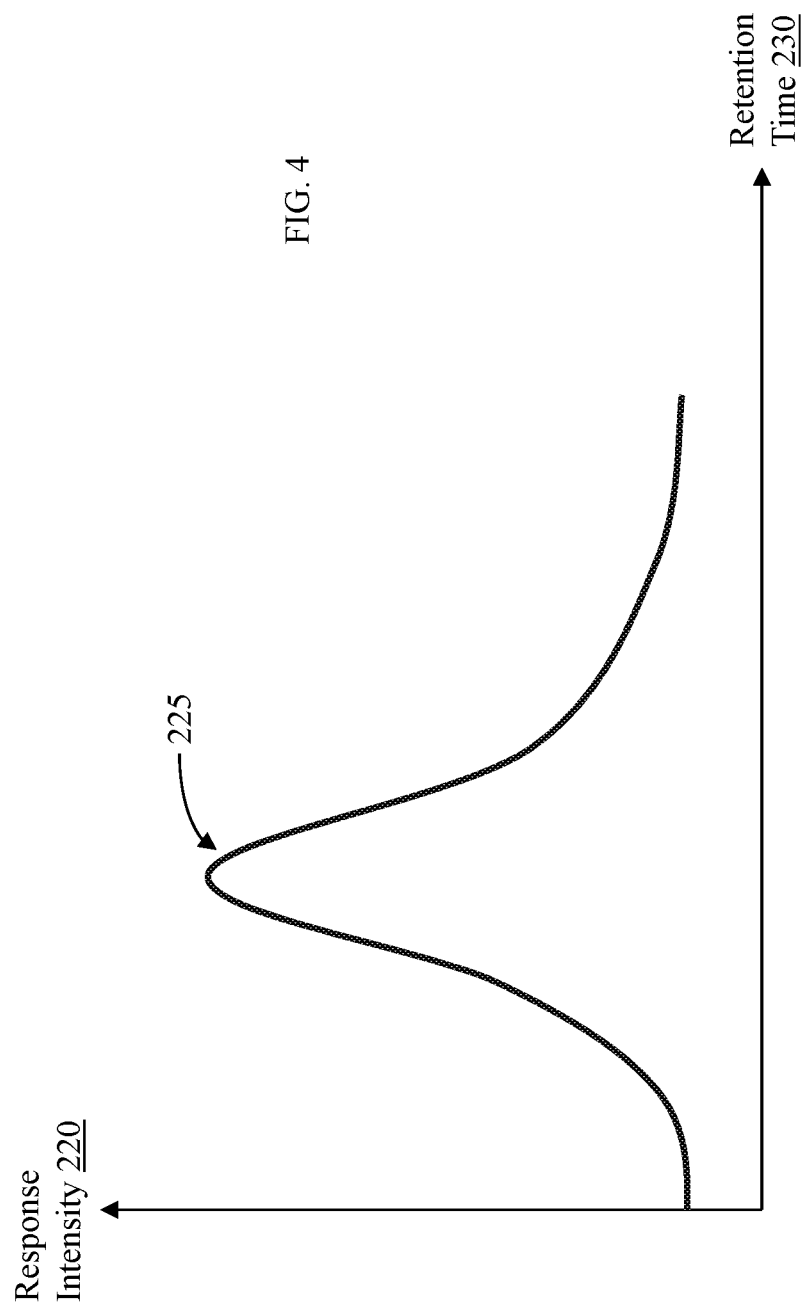
Figure 5:
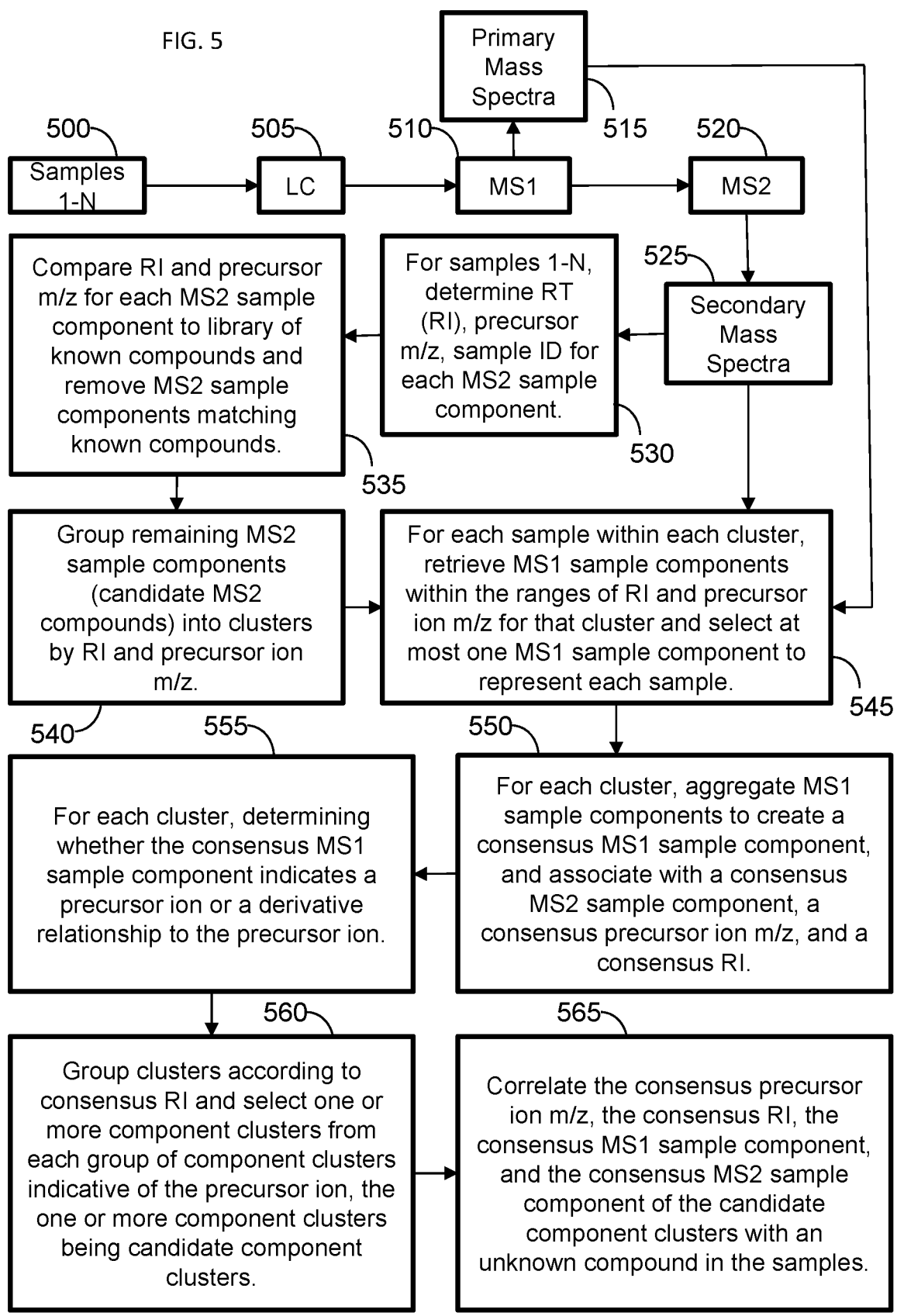

Having thus described the disclosure in general terms, reference will now be made to the accompanying drawings, which are not necessarily drawn to scale, and wherein:

FIG. 1 schematically illustrates a system according to one aspect of the present disclosure including a memory device having a database, a processor device, and a user interface (display), in communication with a spectrometry device;

FIG. 2 schematically illustrates a three-dimensional plot of spectrometry data associated with one exemplary sample;

FIG. 3 schematically illustrates a two-dimensional profile plot for one exemplary sample that may be determined from the corresponding three-dimensional plot of spectrometry data for that sample according to some aspects of the present disclosure;

FIG. 4 schematically illustrates a two-dimensional profile plot for one exemplary sample that may be determined from the corresponding three-dimensional plot of spectrometry data for that sample according to some aspects of the present disclosure; and FIG. 5 schematically illustrates a method of analyzing and discerning small molecule components or compounds of a complex mixture, according to one example aspect of the present disclosure.

DETAILED DESCRIPTION OF THE DISCLOSURE

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Definition of Terms

The terms "compound", "small molecule", "metabolite", or "biochemical" may be used interchangeably and mean organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weight of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates, which can be metabolized further or used to generate large molecules, called macromolecules. The term "small molecules" includes signaling molecules and intermediates in the chemical reactions that transform energy derived from food into usable forms. Non-limiting examples of small molecules include sugars, fatty acids, amino acids, nucleotides, intermediates formed during cellular processes, and other small molecules found within the cell.

The term "Retention Index" or "RI" is a normalized measure of the retention time of a compound in liquid chromatography.

The term "unnamed compound" or "unnamed biochemical" refers to a compound recognized by mass, RI, and MS2 spectrum; its chemical name, molecular formula, and chemical structure are unknown.

The term "tandem MS" refers to an operation in which a first MS step, called the "primary MS" or "MS1", is performed, followed by performance of one or more of a subsequent MS step, generically referred to as "secondary MS" or "MS2". In the primary MS (MS1), an ion, representing one (and possibly more than one) chemical constituent (MS1 sample components), is detected and recorded during the creation of the primary mass spectrum. The substance represented by the ion is subjected to the secondary MS (MS2), in which the substance of interest undergoes fragmentation in order to cause the substance to break into sub-components, which are detected and recorded as a secondary mass spectrum (MS2 sample components). In a true tandem MS, there is an unambiguous relationship between the ion of interest in the primary MS and the resulting peaks created during the secondary MS. The ion of interest in the primary MS corresponds to a "parent" or precursor ion, while the ions created during the secondary MS correspond to sub-components of the parent ion and are herein referred to as "daughter," "child," or "product" ions. Tandem MS allows the creation of data structures that represent the parent-daughter relationship of chemical constituents in a complex mixture. This relationship may be represented by a tree-like structure illustrating the relationship of the parent and daughter ions to each other, where the daughter ions represent sub-components of the parent ion. Tandem MS may be repeated on daughter ions to determine "grand-daughter" ions, for example. Thus, tandem MS is not limited to two-levels of fragmentation but is used generically to refer to multi-level MS, also referred to as "MS$^n$". The term "MS/MS" is a synonym for "MS2".

The term "ionization" is the process by which a neutral molecule becomes a charged ion, by way of the addition or removal of charge subatomic particles (e.g. protons or electrons), which permits MS detection. "Ionization products" are the ions formed by a single molecule or compound in the ionization process.

The term "MS1 spectrum" or "primary mass spectrum" or "MS1 sample components" or "MS1 SC" refers to sample data obtained from a primary mass spectrometry (MS1) analysis.

The term "MS2 spectrum" or "secondary mass spectrum" or "MS2 sample components" or "MS2 SC" refers to sample data obtained from a secondary mass spectrometry (MS2) analysis.

The term "precursor ion mass" refers to the mass of an ion of interest detected in a primary MS (MS1) step.

The term "library" or "ion data repository" refers to a collection of information on compounds detected by mass spectrometry. The information on a compound may include, for example, information related to mass, RI, and MS spectra of the compound. The information may also include information related to various isotopes and adducts of a compound. The library may also include information from public databases such as SMILES strings, Inchi strings, InchiKey, etc.

The terms "derivative relationship" or "mass relationship" refer to a derivative of a molecule of interest that is related to the ionization products of the molecule of interest. Derivative relationships or mass relationships may include in-source fragments, adducts, isotopes, dimers, oligomers, multiple charged species. Derivative relationships or mass relationships may also include more complex relationships, including variations of the described derivative or mass relations, including, for example, adducts of isotopes, oligomers of isotopes, different isotopes of the same molecule.

The various aspects of the present disclosure mentioned above, as well as many other aspects of the disclosure, are described in further detail herein. The apparatuses, methods, and computer program products associated with aspects of the present disclosure are exemplarily disclosed, in some instances, in conjunction with an appropriate analytical device which may, in some instances, comprise a separator portion or separation portion (e.g., a liquid chromatograph, a gas chromatograph, a supercritical fluid chromatograph, or a capillary electrophoresis analyzer) and/or a detector portion (e.g., a spectrometer). One skilled in the art will appreciate, however, that such disclosure is for exemplary purposes only to illustrate the implementation of various aspects of the present disclosure.

Particularly, the apparatuses, methods, and computer program products associated with aspects of the present disclosure can be adapted to any number of processes that are used to generate complex sets of data for each sample (e.g., within a single sample), or over/across a plurality of samples, whether biological, chemical, or biochemical, in nature. For example, aspects of the present disclosure may be used with and applied to a variety of different analytical devices and processes including, but not limited to: analytical devices including a separator portion (or "component separator" or "component separation" portion) comprising a liquid chromatograph (LC), a gas chromatograph (GC), a supercritical fluid chromatograph (SFC), a capillary electrophoresis (CE) analyzer; a cooperating detector portion (or "mass spectrometer" portion) comprising of a nuclear magnetic resonance imaging (NMR) device; a mass spectrometer (MS); an ion mobility spectrometry mass spectrometer (IMS-MS); and an electrochemical array (EC); and/or combinations thereof (e.g., a tandem mass spectrometer including MS1 and MS2).

In some aspects of the present disclosure, the detector portion may be used without a separator portion. In this regard, one skilled in the art will appreciate that the aspects of the present disclosure as disclosed herein are not limited to metabolomics analysis. For example, the aspects of the present disclosure as disclosed herein can be implemented in other applications where there is a need to characterize or analyze small molecules present within a sample or complex mixture, regardless of the origin of the sample or complex mixture. For instance, the aspects of the present disclosure as disclosed herein can also be implemented in a bioprocess optimization procedure where the goal is to grow cells to produce drugs or additives, or in a drug metabolite profiling procedure where the goal is to identify all metabolites that are the result of biotranformations of an administered xenobiotic. Some other non-limiting examples of other applications could include a quality assurance procedure for consumer product manufacturing where the goal may be to objectively ensure that desired product characteristics are met, in procedures where a large number of sample components can give rise to a particular attribute, such as taste or flavor (e.g., cheese, wine or beer), or scent/smell (e.g., fragrances). One common theme thus exhibited by the aspects of the present disclosure as disclosed herein is that the small molecules in the sample can be analyzed using the various apparatus, method and computer program product aspects disclosed herein.

FIG. 1 illustrates an example of a system according to one aspect of the present disclosure wherein the system is in communication with an analytical device 110, such as a combination chromatograph (component separator/component separation)/tandem mass spectrometer (MS1, MS2). One skilled in the art will appreciate, however, that the configurations of an analytical device 110 presented herein are for exemplary purposes only, and are not intended to be limiting with respect to the scope of suitable and appropriate analytical devices that may also be applied under the principles disclosed herein. As shown, a sample (whether biological, chemical, or biochemical, in nature) 100 may be introduced into the separator portion/separation portion of the analytical device 110 and analyzed using appropriate techniques, as applied through the first mass spectrometer (MS1) and the second mass spectrometer (MS2) of the detector portion, that will be appreciated by those skilled in the art.

For example, the components of a particular sample 100 may pass through a column associated with the separator portion/separation portion, at different rates and exhibit different spectral responses (e.g., associated with intensity as a function of retention time), as detected by the first mass spectrometry step (MS1) of the detector portion, based upon their specific characteristics. The second mass spectrometry step (MS2) adds a second phase of mass fragmentation step (MS2) which may be implemented. for example, to facilitate quantitation of low levels of compounds in the presence of a high sample matrix background. As will be appreciated by one skilled in the art, the analytical device 110 may generate a set of spectrometry data, corresponding to each sample 100 and having three or more dimensions (e.g., quantifiable samples properties) associated therewith, wherein the data included in the data set generally indicates the composition (e.g., sample components) of the sample 100. In some aspects, the data set may comprise, for example, data for each sample related to retention time, sample or component (ion) mass (or mass-to-charge ratio), intensity, or even sample indicia or identity. However, such data must first be appropriately analyzed in order to determine the sample composition (e.g., ions, metabolites).

In some instances, a three-dimensional data set (MS1 or MS2) for each of one or more samples may be selected or otherwise designated for further analysis, with each dimension corresponding to a quantifiable sample property. An example of such a three-dimensional set of spectrometry data is shown generally in FIG. 2, and may be plotted on a three-axis plot or graph, with the plot or graph including individual axes for a response intensity element 220, a sample component mass element 210 (or mass-to-charge ratio), and a time element 230 (particularly, in this example, the retention time or the time that a particular component spends in the column of the separator portion of the analytical device 110). That is, the data obtained for a particular sample, in some aspects, includes a relationship between ion mass 210, retention time 230, and intensity 220, including intensity 220 as a function of retention time 230 for a particular ion mass 210. The location of data points in relation to the sample component mass axis 210 may be indicative, for example, of the number of individual component molecules within the sample 100 and the relative mass values for such sample components.

According to other aspects of the present disclosure, different analytical devices may be used to generate a three or more dimensional set of analytical data corresponding to the sample 100. For example, the analytical device may include, but is not limited to: various combinations of a separator portion/separation portion comprising one of a liquid chromatograph (LC) (positive or negative channel) and a gas chromatograph (GC), a supercritical fluid chromatograph (SFC), a capillary electrophoresis (CE) analyzer; and a cooperating detector portion comprising one of a nuclear magnetic resonance imaging (NMR) device; a mass spectrometer (MS); an ion mobility spectrometer (IMS), a tandem mass spectrometer (MS1 and MS2); and an electrochemical array (EC). In some aspects, the analytical device may include a detector portion without a separator portion. One skilled in the art will appreciate that such complex three or more dimensional data sets may be generated by other appropriate analytical devices that may be in communication with components of aspects of the present disclosure as described in further detail herein.

One or more samples 100 may be taken individually from a well plate 120 and/or from other types of sample containers and introduced individually into the analytical device 110 for analysis and generation of the corresponding three or more dimensional data set (see, e.g., FIG. 2). For example, individual samples 100 may be transferred from a well plate 120 to the analytical device 110 via pipette, syringe, microfluidic passageways defined by a test array, and/or other systems for transferring samples in a laboratory environment. As disclosed herein, the nature of the samples may vary considerably, generally comprising mixtures or complex mixtures including small molecules, wherein such samples may exemplarily include, but are not limited to: blood samples, urine samples, cell cultures, saliva samples, plant tissue and organs (e.g., leaves, roots, stems, flowers, etc.), plant extracts, culture media, membranes, cellular compartments/organelles, cerebral spinal fluid (CSF), milk, soda products, food products (e.g., yogurt, chocolate, juice), and/or other types of biological, chemical, and/or biochemical samples in which the metabolites and/or chemical/molecular components of interest may be present. Of these possible samples or sample types, one common aspect is that the selected sample includes a MS1 and/or MS2 sample component. Empirical data or other information associated with the MS1 and/or MS2 sample component of the sample may be implemented to determine, for example, one or more ions, small molecules or metabolites expected to be present in such a sample having that MS1 and/or MS2 sample component. That is, such information associated with the MS1 and/or MS2 sample component provides a context to the sample and the data obtained therefrom via the component separation and mass spectrometer system, wherein the context provides an indicium or indicia at least as to a basic component or constituent of the sample.

As shown in FIG. 1, aspects of the present disclosure may comprise an ion data repository (e.g., a library) comprising, for example, a database (e.g., a relational database) stored at least in part, for example, as executable or accessible instructions in a memory or memory device 140 (i.e., a computer-readable storage medium having computer-readable program code portions stored therein), wherein the memory device 140 is in communication with a processor or processor device 130 (e.g., a computer device implementing a processor) for selectively executing the instructions/computer-readable program code portions in the memory device 140 to cause an apparatus to perform particular method steps and/or functions. In some instances, the memory device 140 and/or the processor device 130 may be configured to be in communication, whether directly or indirectly, with the analytical device 110 for receiving a data set (in some instances, a data set comprising three or more dimensions, wherein a data parameter such as sample indicia, sample or component (ion) mass, retention time, and intensity/response may represent any one of the dimensions of the data set), corresponding to the sample 100, therefrom. That is, the dataset received by the memory device includes, for example, data indicating a relationship between ion mass (or ion mass-to-charge ratio), retention time, and intensity. In some particular instances, the dataset (for each of one or more samples 100) includes data indicating intensity as a function of retention time for a particular ion mass. The processor device 130 may be in communication with the analytical device 110 via wire line (RS-232, and/or other types of wire connection) and/or wireless (such as, for example, RF, IR, or other wireless communication) techniques such that the database associated with the memory device 140/processor device 130 (and/or in communication therewith) may receive the data set from the analytical device 110 so as to be stored thereby.

Furthermore, the analytical device 110 may be in communication with one or more processor devices 130 (and associated user interfaces and/or displays 150) via a wire line and/or wireless computer network including, but not limited to: the Internet, local area networks (LAN), wide area networks (WAN), or other networking types and/or techniques that will be appreciated by one skilled in the art. The user interface/display 150 may be used to receive user input and to convey output such as, for example, displaying any or all of the communications involving the system, including the manipulations and analyses of sample data disclosed herein, as will be understood and appreciated by one skilled in the art. The database may be structured using commercially available software, such as, for example, Oracle, Sybase, DB2, or other database software. As shown in FIG. 1, the processor device 130 may be in communication with the user interface/display 150 and the memory device 140 (such as a hard drive, memory chip, flash memory, RAM module, ROM module, and/or other memory device 140) for storing/administering the ion data repository/database, including the data sets received from the analytical device 110, whether automatically (directly) or indirectly. In addition, the memory device 140 may also be used to store other received data or information involving the sample(s) or component(s) thereof in the ion data repository/database and/or data otherwise manipulated by the processor device 130.

The processor device 130 may, in some aspects, be capable of converting each of the data sets, each including, for example, data indicating a relationship between various sample parameters such as ion mass, retention time, and intensity (see, e.g., FIG. 2, wherein the exemplary data set is a three-dimensional data set) for each of the samples, received by the memory device 140, into at least one corresponding two-dimensional data set (see, e.g., FIG. 3). The at least one two-dimensional data set may comprise, for example, a two-dimensional component "profile" of a particular sample 100 at a particular point 235 (FIG. 2) along one of the three axes of the three-dimensional data set. The particular point 235 along one of the three axes may be, for example, a particular selected sample component mass along the sample component mass axis 210. Once that particular sample component mass is selected, the resulting "slice" of the three-dimensional data set becomes the two-dimensional profile plot for the sample. That is, the resulting profile (also referred to herein as a "profile plot" as shown in FIGS. 3 and 4) illustrates that particular sample component mass detected (and the intensity of that detection) as a function of time measured from a zero point, the zero point corresponding to when the sample 100 is injected and/or otherwise introduced into the analytical device 110). For example, the processor device 130 may be configured to produce a detection intensity/response versus/as a function of sample component (retention) time two-dimensional profile of the sample for that given or selected sample component mass point 235 (see FIGS. 3 and 4, for example). The "x" axis in FIG. 2 (or (retention) time axis 230, for example) may further, in some instances, be characterized as a retention index (e.g., the retention time of an ion/compound normalized to the retention times of adjacently eluting known ions/compounds) and/or a retention time. Thus, the processor device 130 may be further capable of parsing each of the three (or more) dimensional data sets, for each of the plurality of samples, into one or more individual two-dimensional (i.e., intensity/response versus sample component retention time profile) profiles corresponding to at least one particular (selected) sample component mass point (element 235, for example) so as to convert each three (or more) dimensional data set (of FIG. 2, for example) into at least one corresponding two-dimensional data set of a selected sample component (having a profile or profile plot shown, for example, in FIGS. 3 and 4) that may further be plotted as an response intensity 220 of the corresponding sample component mass versus a sample component retention time 230 (or retention index), and displayed on the user interface/display 150, as desired. One skilled in the art will appreciate that any amount of two-dimensional data sets or profile plots may be formed or obtained from any three or more dimensional data sets by selecting two different sample parameters at a selected particular value of a third sample parameter, and then plotting the two different sample parameters against each other in a two-dimensional plot.

According to some aspects, the processor device 130 may be configured to selectively execute the executable instructions/computer-readable program code portions stored by the memory device 140, if necessary, in cooperation with the ion data repository/library/database also stored by the memory device 140, so as to accomplish, for instance, the identification, quantification, representation, curation, and/or other analysis of a selected sample component (i.e., a metabolite, molecule, or ion, or portion thereof) in each of the plurality of samples (or within a single sample), from the two-dimensional data set representing the respective sample among the plurality of samples.

According to particular aspects, as shown in FIG. 5, a method of analyzing data for one or more samples (Block 500) is provided, with the data for each sample being obtained from a component separation and tandem mass spectrometer system comprising a separation portion (Block 505), including a liquid chromatograph, a gas chromatograph, a supercritical fluid chromatograph, or a capillary electrophoresis analyzer, and a first mass spectrometry step or provision (MS1) (Block 510) and a second mass spectrometry step or provision (MS2) (Block 515), wherein the data from the MS1 includes MS1 sample components (primary mass spectra—Block 520) and the data from the MS2 includes MS2 sample components (secondary mass spectra—Block 525).

Such a method comprises analyzing, for each sample, a data set for a plurality of MS2 sample components to determine a precursor ion mass-to-charge ratio (m/z) and a retention index (RI) for each MS2 sample component (Block 530). The precursor ion m/z and the RI for each MS2 sample component is compared to precursor ion mass-to-charge ratios and retention indices of known compounds, and any MS2 sample component corresponding to one of the known compounds removed from the data set (Block 535). Remaining MS2 sample components in the data set are candidate MS2 sample components.

Component clusters are formed across the candidate MS2 sample components, with each component cluster including candidate MS2 sample components each having the precursor ion m/z and the RI within respective ranges for the component cluster (Block 540). For each sample within each component cluster, one or more MS1 sample components within the respective precursor ion m/z and RI ranges for the component cluster is retrieved. For each component cluster, at most one consensus MS1 sample component is determined by aggregating the one or more MS1 sample components within the respective precursor ion m/z and RI ranges, and the consensus MS1 sample component represents each sample (Block 545). The consensus MS1 sample component is associated with a corresponding consensus MS2 sample component, consensus precursor ion m/z, and consensus RI determined by aggregating the MS2 sample components and associated precursor ion m/z and the RI within the component cluster (Block 550). For each component cluster, it is determined whether the consensus MS1 sample component indicates a molecular ion or a derivative relationship to the molecular ion (Block 555). Component clusters are grouped according to consensus RI, and one or more component clusters selected from each group of component clusters, with the one or more component clusters being candidate component clusters (Block 560). The consensus precursor ion m/z, the consensus RI, the consensus MS1 sample component, and the consensus MS2 sample component of the candidate component clusters are then correlated with an unknown compound in the samples (Block 565).

Alternately stated, such a method comprises, for each sample, analyzing a data set for a plurality of MS2 sample components to determine a retention index and a precursor ion mass for each MS2 sample component. The retention index and precursor ion mass for each MS2 sample component is compared to retention indices and precursor ion masses of known compounds, and any MS2 sample component corresponding to one of the known compounds removed from the data set. The remaining MS2 sample components in the data set are candidate MS2 sample components. Such a method further comprises forming component clusters across the candidate MS2 sample components, with each component cluster including candidate MS2 sample components having the retention index and the precursor ion mass within respective ranges. For each component cluster, one or more MS1 sample components is retrieved having a retention index and a precursor ion mass within the respective retention index and precursor ion mass ranges. At most one MS1 sample component is selected from the one or more MS1 sample components having the retention index and precursor ion mass within the respective retention index and precursor ion mass ranges. Such a method additionally comprises comparing the selected at most one MS1 sample component for each component cluster, across the component clusters, to determine whether the selected at most one MS1 sample component is a precursor ion or is a mass relationship of the precursor ion. For the selected at most one MS1 sample component being the precursor ion, a molecular mass thereof within the precursor ion mass range of the component cluster is determined, as well as an associated retention index of the precursor ion. Candidate component clusters are formed from candidate MS2 sample components having the retention index and the precursor ion mass corresponding to the determined molecular mass and the associated retention index of the precursor ion, with each candidate component cluster being associated with a candidate unknown compound.

In some aspects, removing any MS2 sample component from the data set corresponding to one of the known compounds comprises removing any of a known molecular ion, a background artifact, a chromatographic artifact, or a derivative relationship of the known molecular ion, a mass relationship of the known molecular ion, the background artifact, or the chromatographic artifact, corresponding to one of the known compounds, from the data set. In other aspects removing the derivative relationship of the known molecular ion or the mass relationship of the known molecular ion from the data set comprises removing any of an in-source fragment, an adduct, an isotope, a dimer, an oligomer, a multiple charged species, an adduct of an isotope, or an oligomer of an isotope, from the data set.

In some aspects, such a method comprises determining precursor ion mass-to-charge ratios and retention indices of the known compounds from the MS1 sample components thereof.

In further aspects, such a method comprises associating any of the precursor ion m/z, the RI, the MS1 sample components, and the MS2 sample components of each known compound with the respective known compound in a database comprising an ion data repository, and/or comprises associating the precursor ion m/z, the RI, MS1 sample components, and the MS2 sample components of each candidate component cluster with the unknown compound in a database comprising an ion data repository.

In some aspects, such a method comprises determining the retention index by normalizing a retention time for each MS2 sample component.

In some aspects, forming component clusters across the candidate MS2 sample components comprises forming component clusters across the candidate MS2 sample components using divisive clustering or agglomerative clustering.

In some aspects, such a method comprises sorting the candidate MS2 sample components by precursor ion mass prior to forming the component clusters across the candidate MS2 sample components.

In some aspects, such a method comprises sorting the component clusters by retention index to generate secondary component clusters.

In some aspects, the step of forming component clusters across the candidate MS2 sample components is repeated two or more times.

In some aspects, comparing the consensus MS1 sample component for each component cluster, across the component clusters, is performed across a plurality of the samples.

In some aspects, such a method comprises removing any component clusters that are present in less than 5% of the plurality of samples.

In some aspects, such a method comprises analyzing a plurality of possible derivative relationships or possible mass relationships of the MS1 sample components prior to associating the consensus MS1 sample component with a corresponding consensus precursor ion m/z.

In some aspects, analyzing the plurality of possible derivative relationships or the plurality of possible mass relationships comprises analyzing the plurality of possible derivative relationships or possible mass relationships using symbolic algebra in a single run to generate computer code for analyzing a set of specified derivative relationships or mass relationships.

In some aspects, such a method comprises removing any component clusters lacking a plausible molecular formula, prior to grouping the component clusters, while other aspects comprise removing any component clusters lacking statistical significance from metadata of the data of the one or more samples being analyzed, prior to grouping the component clusters.

In some aspects, such a method comprises prioritizing candidate component clusters having statistical significance with respect to metadata of the data of the one or more samples being analyzed as candidate unknown compounds.

Some aspects further comprise an apparatus for analyzing data for one or more samples, the data for each sample being obtained from a component separation and tandem mass spectrometer system comprising a separation portion, including a liquid chromatograph, a gas chromatograph, a supercritical fluid chromatograph, or a capillary electrophoresis analyzer, and a first mass spectrometry step or provision (MS1) and a second mass spectrometry step or provision (MS2), wherein the apparatus comprises a processor and a memory storing executable instructions that, in response to execution by the processor, cause the apparatus to at least perform the method steps of any preceding example aspect or combinations thereof disclosed herein.

Some aspects further comprise a computer program product for analyzing data for one or more samples, the data for each sample being obtained from a component separation and tandem mass spectrometer system comprising a separation portion, including a liquid chromatograph, a gas chromatograph, a supercritical fluid chromatograph, or a capillary electrophoresis analyzer, and a first mass spectrometry step (MS1) and a second mass spectrometry step (MS2), wherein the computer program product comprises at least one non-transitory computer readable storage medium having computer-readable program code stored thereon, wherein the computer-readable program code comprises program code for performing the method steps of any preceding example aspect or combinations thereof disclosed herein.

In some aspects, the retention indices and precursor ion masses of known compounds may be generated by MS1. In another aspect, the retention indices and precursor ion masses of known compounds may be stored in a database. In yet another aspect, the database may be an ion data repository.

In some aspects, the component clusters may be formed by a clustering technique such as divisive clustering or agglomerative clustering.

In some aspects, the candidate MS2 sample components used to form the component clusters may be sorted by precursor ion mass prior to forming the component clusters. In another aspect, the component clusters may also be sorted by retention index. The component clusters may be sorted first by precursor ion mass and then by retention index. Alternatively, the component clusters may be sorted first by retention index and then by precursor ion mass. The component clusters may be repeatedly sorted and divided into progressively smaller component clusters.

In some aspects, the process of comparing the selected MS1 sample component across component clusters may be performed across a plurality of samples. In other aspects, when this comparison is performed across a plurality of samples, component clusters that are only present in a few samples may be removed. For example, component clusters that are present in less than 5% of the plurality of samples may be removed from analysis.

In some aspects, mass relationships of the MS1 sample components may be analyzed prior to selecting the molecular mass corresponding to the precursor ion mass range of the component cluster. In one example, 500 or more mass relationships may be analyzed. In another example, 1,000 or more mass relationships may be analyzed. In yet another example, 1,500 or more mass relationships may be analyzed. That is, such a method may also include analyzing a plurality of possible mass relationships of the MS1 sample components prior to determining the molecular mass of the precursor ion within the precursor ion mass range of the component cluster. In this aspect, symbolic algebra software may be used in a computer program product to perform the analysis. In another aspect, the symbolic algebra software may be run a single time to generate computer codes to analyze a set of specified mass relationships. That is, in some aspects, analyzing the plurality of possible mass relationships comprises analyzing the plurality of possible mass relationships using symbolic algebra in a single run to generate computer code for analyzing a set of specified mass relationships.

In some aspects, component clusters may be further evaluated prior to forming candidate component clusters. In an example of such aspects, component clusters may be evaluated based on molecular formula, and component clusters that do not have a plausible molecular formula may be removed from the analysis. In another example of such aspects, component clusters may be evaluated based on statistical significance with respect to the metadata of the study under consideration. If the component clusters are not determined to be statistically significant based on the metadata of the study under consideration, then the component clusters may be removed from the analysis. That is, in various aspects, the method may further include removing any component clusters lacking a plausible molecular formula, prior to forming the candidate component clusters; or removing any component clusters lacking statistical significance from metadata of the data being analyzed, prior to forming the candidate component clusters.

In some aspects, the method may be performed on a single sample.

In some aspects, the candidate component clusters may be prioritized as candidate unknown compounds based on statistical significance with respect to the metadata of the study under consideration. That is, such a method may further comprise prioritizing candidate component clusters having statistical significance with respect to metadata of the data being analyzed as candidate unknown compounds. In a feature of such an aspect, a candidate component cluster having a high statistical significance may be given high priority as a candidate unknown compound. In another feature of such an aspect, a candidate component cluster having a low statistical significance may be given a lower priority as a candidate unknown compound.

In some aspects, the list of candidate unknown compounds generated by the method as well as their associated candidate component clusters may be stored in a database for future analysis.

In some aspects, there is information associated with the candidate unknown compound. The information associated with the candidate unknown compounds may include precursor ion mass, retention index, MS1 sample components, and MS2 sample components.

Inputs and Outputs:

The input to the method, apparatus, and computer program product of the present disclosure is the chromatographic and mass spectrometer data from one or more samples. In particular aspects, the data is obtained from a liquid chromatograph/tandem mass spectrometer (LC-MS/MS) system. The output is a set of candidate, unnamed compounds, not previously present in an ion data repository, that are present in the one or more samples. The output also includes mass (or mass-to-charge ratio m/z), retention index (or RI), and MS2 spectrum (or MS2 sample components). Secondarily, the output includes plausible molecular formulas, and a table of possible isotopes, adducts, and oligomers for each component cluster.

Applications:

In one application, the samples may be from an experimental study such as a case-control study or a longitudinal study in which statistical tests such as ANOVA or Welch's t-test can be applied to peak areas of candidates using available metadata for the samples to identify statistically significant candidates.

In another application, the samples may come from a previously un- or under-studied matrix type such as dried blood spots, and the goal may be to identify any new features that occur in most or all samples. In another application, there may be a single unique sample, with the goal of identifying and detecting new compounds in the single unique sample.

In another application, the samples may originate from laboratory processes (such as water process blanks), and the goal may be to identify new contaminants Method Steps:
1. Read raw MS files, collecting, for each MS2 scan, a pair consisting of the mass-to-charge ratio (m/z) and retention time (RT) corresponding to the precursor of the MS2 scan (i.e., the ion fragmented in MS2). Normalize retention times in a manner to facilitate alignment of corresponding scans in different samples, giving a pair (RI, m/z), where RI ("retention index") represents normalized retention time. Retention times may be normalized in various ways, but in one embodiment, retention times are normalized by a piece-wise linear interpolation between known compounds "spiked into" each sample for calibration.
2. Discard pairs that match any entry in the existing MS1 library, whether molecular ion, adduct, isotope, or other derivative.
3. Cluster remaining pairs into features that are compact in (RI, m/z) space by any of a number of clustering algorithms known to those skilled in the art, including but not limited to K-Means, Hierarchical Clustering, Agglomerative Clustering, DBSCAN, Gaussian Mixtures, or Birch Clustering. In one aspect, clustering may be performed by a divisive clustering algorithm as in the following example:
    a. Place all pairs in a single large cluster.
    b. Sort all pairs by m/z, and divide into groups wherever there is a large gap in m/z.
    c. Sort each group by RI and divide it into smaller groups wherever there is a large gap in RI.
    d. Sort each group by m/z and divide into smaller groups at large m/z gaps.
    e. Sort each group by RI again and divide at large RI gaps.
    f. Discard groups that are too small, that have too wide a span in m/z space (e.g., >5 ppm), or that have too wide a span in RI space (e.g., 250 units)
    The groups at the end of this process are "features."
4. Retrieve all integrated peaks from a (MS1) database of integrated peaks previously derived from the samples that lie within the range of (RI, m/z) space occupied by the feature.
5. For each feature and sample, choose a "best" peak from among those retrieved. The best peak will be nearest to an aggregate RI based on the set of all peaks.
6. Discard features for which too few samples have a peak (e.g., require that 5% of samples have a peak).
7. Discard features whose m/z has no plausible molecular formula, using precomputed tables as described below.
8. Optionally, compute the statistical significance of the peak areas of each feature with respect to available metadata. This step uses, e.g., a bespoke code module for each study. Discard insignificant features.
9. Reread raw MS1 and MS2 files and collect necessary spectra to complete analysis of each feature:

a. Initialize an empty collection of the 'best' MS1 and MS2 spectra for each feature. The size of these collection can be limited to 20-50 as an implementation parameter.
b. Read raw files one by one:
   i. Collect all spectra for the sample.
   ii. For each feature, find the spectra underneath the corresponding peak in the sample. If these spectra are among the best seen so far, add them to the feature's collections, removing any spectra that have become superfluous. The 'best' spectra will be those with highest intensity for the feature ion. This incremental strategy is important for memory management (e.g., all spectra are not stored/retained until all samples are read).
10. Perform MS1 analysis for each feature:
   a. Transform each ion in each MS1 spectrum into a (delta, ratio) pair. Delta is the difference between the m/z of the ion and the m/z of the precursor ion in the same spectrum. m/z=mass-to-charge ratio, and ratio is the ratio between the intensity of the ion and the intensity of the precursor ion in the same spectrum.
   b. Use the mass of the precursor to construct a large table of deltas of possible adductive, isotopic, and oligomeric relationships. The computer code that constructs this table will have been constructed automatically using symbolic algebra as outlined below.
   c. Assign each (delta, ratio) pair to a nearby delta (e.g., ±1 ppm) in the table of possible relations. These pairs will support the existence of the corresponding relationship in the spectrographic data.
   d. Considering the set of assigned pairs for each possible relationship, determine if there are a sufficient number of pairs and if the ratios fall in a narrow range. If so, report the relationship.
   e. In addition, if the relationship is isotopic, such as, for example, $^{13}C$, $^{37}Cl$, $^{81}Br$, or $^{34}S$, use the median ratio of intensities to predict the number of C, Cl, Br, or S in the feature ion based on the binomial distribution and natural abundances of isotopes.
   f. Consider any pairs that were unassigned in (c), and cluster by delta. If any cluster includes a large number of pairs and its ratios are similar, report this as a possible relationship of unknown origin.
The output of Step 10 is a table of isotopic, adductive, oligomeric, and undescribed relationships between the feature ion and co-occurring ions.
11. Perform MS2 analysis for each feature (i.e., construct the MS2 spectrum):
   a. Cluster the set of all MS2 ions into subsets of ions of possibly equal exact m/z according to the errors in measurement typical of the instrument. In one example, m/z space between 50 u and 1000 u may be divided into approximately 300,000 bins of width 5 ppm, each ion (m/z, intensity) pair may be assigned to a bin according to m/z, and each subset consists of all ions assigned to the same or adjacent bins.
   b. Find the "normalizing" ion subset: In one preferred aspect, the normalizing ion is the most intense ion in each MS2 spectrum, but this may not always be so. In each MS2 spectrum, rank the subsets by the intensity of the ion(s) they contain, smallest to largest. Sum the ranks for each subset. The subset with largest sum becomes the normalizer.
   c. In each MS2 spectrum, divide all intensities by the intensity of the normalizer in the same MS2 spectrum to get relative intensities.
   d. Aggregate relative intensities for each subset. Eliminate subsets with too few intensities as noise.
   e. Find the median m/z and median relative intensity for each subset. Report these as the consensus MS2 spectrum.
The output of Step 11 is a proposed MS2 spectrum for the candidate compound.

Finding Plausible Molecular Formulas Using Precomputed Tables

A plausible molecular formula is one in which the sum of the masses of the individual atoms is the same as the mass of the feature. A common approach to this problem is the one taken, for example, by the ChemCalc website, which, when given a mass query, computes a set of formulas on the fly, evidently using a Branch-and-Bound approach. This approach is adequately efficient for a small number of queries, and it is flexible in that parameters of the search (e.g., maximum number of C) can be specified with each query. However, in the present methodology, search parameters can be fixed for greater speed required for a larger number of queries. This permits precomputation of a large table (in ~10 minutes, but only once—not on every run) and makes very fast lookups in that table to answer the queries For the purposes of the present disclosure, a formula that includes Einsteinium is not plausible. Nearly every compound in a current library consists of only C, H, N, O, P, S, Cl, F, I, and Br. Since masses of >1000 u are not considered, the compounds of interest include:

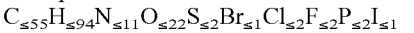

However, this is a set of 56*95*12*23*3*2*3*3*3*2=475,735,680 possible formulas. As such, in practicality, it is not possible to simply enumerate all these formulas and choose those with matching mass.

Generally, formulas with, for example, both I and Cl are not necessarily of interest, and analysis of the existing library shows that, in some instances, it will suffice to consider formulas including:

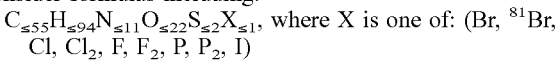

This is a set of 56*95*12*23*3*10=44,049,600 formulas ($^{81}Br$ is included because it is nearly as abundant as $^{79}Br$, and a $^{81}Br$ isotope could reasonably be measured in practice.). Each of these 44 million formulas can be encoded in fewer than 32 bits, and the set then occupies around 150 Mb. The software methodology is:
1. Precomputation (at software build time, i.e., only once)
   A. Enumerate all 44,049,600 formulas.
   B. Compute exact mass of all formulas.
   C. Sort formulas by mass.
   D. Encode each formula in 32 bits.
   E. Store the sorted formulas in a file, possibly including an indexing structure for a sorted list. (Many suitable indexing structures are in common use.)
2. Search (for many masses in every run)
   A. Find the upper and lower limits of exact mass corresponding to a given accurate mass.
   B. Use the stored indexing structure (or binary search) to find encoded formulas of appropriate exact mass.
   C. Decode and return formulas.

Finding MS1 Relationships Using Automatically Generated Code

Aspects of the present disclosure provide the ability to efficiently analyze a theoretically unlimited number of previously specified relationships between m/z of a precursor ion and other MS1 ions. These relationships include not just isotopes, adducts, multiply charged species and oligomers, but more complex mass relationships such as adducts of isotopes, oligomers of isotopes, different isotopes of the same molecule (e.g., $^{13}C$ and $^{37}Cl$ isotopes), and other derivatives of the precursor ion. In one example, 500 or more mass relationships are analyzed. In another example, 1,000 or more mass relationships are analyzed. In another example, 1,500 or more mass relationships are analyzed. The ability to efficiently analyze large numbers of mass relationships is accomplished by building, for each feature mass, a table of many rows, each of which describes one possible relationship, keyed on the delta associated with that relationship. The table is built by passing the feature mass to a function in the software. This table will be different for every feature mass; the delta for a dimer is clearly different for a feature mass of 300 (i.e., about 300) and a feature mass of 500 (i.e., about 500).

It would be tedious and error-prone for a human to perform the algebra necessary to write computer codes to evaluate such a large number of relationships, since a symbolic (rather than numerical) solution must be found for one or algebraic equations for each relationship. The writing of the function itself can be automated using a symbolic algebra software system. A symbolic algebra software system accepts equations and other mathematical expressions encoded as character strings, and then solves the equations symbolically. For example, if told "solve 2z=x+y; y=x+2 for z", the result would be not a number, but the symbolic result "z=x+1". In the following, m represents the mass of the (uncharged/neutral) precursor biochemical giving rise to (some of) the ions in a hypothetical MS1 scan, and negative ionization is used for concreteness. Note that m is not the mass of the precursor ion. That is, in fact, exactly the point: one goal is to know if the precursor ion is really the "principal ion" (biochemical minus proton), or an adduct or other derivative of the principal ion. Some examples of the use of symbolic algebra are as follows:

Suppose having the principal ion (m−H) for the precursor, and another ion is the $^{13}C$ isotope. In algebraic terms, p=m−H describes the mass of the precursor. (In this discussion H is always the mass of a proton, not a hydrogen atom. In the library, the isotopic ion is described as (m−H[C13−1]), meaning x=m−H+$^{13}C$−$^{12}C$ describes the other ion. In this case:

delta=$x-p=(m-H+^{13}C-^{12}C)-(m-H)$=1.003355, so the table must contain this row:

(precursor='m−H', other='m−H[C13−1]',
delta=1.003355)

A slightly harder case is if the precursor is a dimer, (2m−H), and the other ion is the molecular ion (m−H). Algebraically, $p=2m-H$ $x=m-H,$ so delta=$x-p=--m.$ This time the result is a symbolic result, so the function will create a table with a row with a symbolic expression for delta. When the function is called during the analysis of a particular feature, the variables in the symbolic expression for delta will be assigned values, and delta becomes a numerical value.

The function builds a table for the analysis based on the mass of the precursor, not the molecular mass (which is unknown), so delta is expressed in terms of p. In this case, m=(p+H)/2, and the table needs this row:

(precursor='2m−H', other='m−H', delta=−p/2+
0.50364)

Lastly, a more complex example: the precursor is the double-charged $^{13}C$ isotope (m−2H[C13−1])/2, and the other ion has a loss of $CO_2$, denoted by m−H−CO2. In algebraic form:

$p=(m-2H+1.003355)/2$ $x=(m-H-12-2*15.999)$ delta=$x-p=(m/2)-44.4997$ $m=2p+1.0112$ delta=$p-43.994$ The table must contain this row:

(precursor='(m−2H[C13−1])/2', other='m−H−CO2',
delta=$p-43.994$)

Now the problem remains of translating a species notation into normal algebraic expressions. At software build time (i.e., only once), the decision must be made as to which relationships (pairs of molecular species) will be of interest in the MS1 data analysis. Implausible relationships slow processing times and may lead to false positives, especially for larger precursor masses. Then a program is run once, which itself writes computer code to efficiently evaluate many hypothetical relationships between precursor and other ions in the MS1 data.

Application of the Outputs

One goal is to produce a library entry consisting of m/z, RI, MS1 spectrum, and MS2 spectrum, thus identifying plausible molecular formulas, adducts, isotopes, and oligomers.

Having a plausible molecular formula is important for several reasons. If none exists, this hints that the feature is not the molecular (m+H or m−H) ion—perhaps an isotope or oligomer, or perhaps simply noise. Also, if the MS1 data analysis repeatedly labels the feature as something other than the molecular ion, that also weighs against the creation of a library entry. Finally, metabolites are C-rich, so any moderately large metabolite should display a $^{13}C$ ion unless the intensity of the precursor ion is very low.

EXAMPLE

In one example, the methodology was used to analyze 59 mouse plasma samples. These samples came from three groups of mice corresponding to three genotypes at the HAL (histidine ammonia lyase) locus: reference (REF), heterozygous (HET), or knockout (VAR).

To evaluate the validity of the proposed compounds, 15 of the compounds were subjected to detailed manual review by a human expert. This evaluation showed that 11 out of 15 compounds (73.3%) were likely true novel compounds.

Aspects of the present disclosure thus provide methods of analyzing metabolomics data from a LC/tandem MS system, as disclosed herein. In addition to providing appropriate apparatuses and methods, aspects of the present disclosure also provide associated computer program products for performing the functions/operations/steps disclosed herein, in the form of, for example, a non-transitory computer-readable storage medium (i.e., memory device 140, FIG. 1) having particular computer-readable program code portions stored therein by the medium that, in response to execution by the processor device 130, cause the apparatus to at least perform the steps disclosed herein. In this regard, it will be understood that each block or step of the methodology or combinations of blocks/steps in the methodology can be implemented by appropriate computer program instructions executed by the processor device 130. These computer program instructions may be loaded onto a computer device or other programmable apparatus for executing the functions specified in the methodology or otherwise associated with the method(s) disclosed herein. These computer program instructions may also be stored in a computer-readable memory (i.e., memory device 140), so as to be accessible by a computer device or other programmable apparatus in a particular manner, such that the executable instructions stored in the computer-readable memory may produce or facilitate the operation of an article of manufacture capable of directing or otherwise executing the instructions which implement the functions specified in the methodology or otherwise associated with the method(s) disclosed herein. The computer program instructions may also be loaded onto a computer device or other programmable apparatus to cause a series of operational steps to be performed on the computer device or other programmable apparatus to produce a computer-implemented process such that the instructions executed by the computer device or other programmable apparatus provide or otherwise direct appropriate steps for implementing the functions/steps specified in the methodology or otherwise associated with the method(s) disclosed herein. It will also be understood that each step of the methodology, or combinations of steps in the methodology, can be implemented by special purpose hardware-based computer systems which perform the specified functions or steps, or combinations of special purpose hardware and computer instructions (software).

Many modifications and other embodiments of the inventions set forth herein will come to mind to one skilled in the art to which these disclosed embodiments pertain having the benefit of the teachings presented in the foregoing descriptions and the associated drawings. Therefore, it is to be understood that embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure. In this regard, for example, different combinations of elements and/or functions than those explicitly described above are also contemplated within the scope of the disclosure. Although specific terms are employed herein, they are used in a generic and descriptive sense only and not for purposes of limitation It should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

That which is claimed:

1. A method of analyzing data for one or more samples, the data for each sample being obtained from a component separation and tandem mass spectrometer system comprising a separation portion, including a liquid chromatograph, a gas chromatograph, a supercritical fluid chromatograph, or a capillary electrophoresis analyzer, and a first mass spectrometry step or provision (MS1) and a second mass spectrometry step or provision (MS2), wherein the data from the MS1 includes MS1 sample components and the data from the MS2 includes MS2 sample components, said method comprising:

analyzing, for each sample, a data set for a plurality of MS2 sample components to determine a precursor ion mass-to-charge ratio (m/z) and a retention index (RI) for each MS2 sample component;

comparing the precursor ion m/z and the RI for each MS2 sample component to precursor ion mass-to-charge ratios and retention indices of known compounds and removing any MS2 sample component from the data set corresponding to one of the known compounds, with remaining MS2 sample components in the data set being candidate MS2 sample components;

forming component clusters across the candidate MS2 sample components, each component cluster including candidate MS2 sample components each having the precursor ion m/z and the RI within respective ranges for the component cluster;

for each sample within each component cluster, retrieving one or more MS1 sample components within the respective precursor ion m/z and RI ranges for the component cluster;

for each component cluster, determining at most one consensus MS1 sample component, by aggregating the one or more MS1 sample components within the respective precursor ion m/z and RI ranges, to represent each sample, and associating the consensus MS1 sample component with a corresponding consensus MS2 sample component, consensus precursor ion m/z, and consensus RI determined by aggregating the MS2 sample components and associated precursor ion m/z and the RI within the component cluster;

for each component cluster, determining whether the consensus MS1 sample component indicates a molecular ion or a derivative relationship to the molecular ion;

grouping component clusters according to consensus RI and selecting one or more component clusters from each group of component clusters, the one or more component clusters being candidate component clusters; and correlating the consensus precursor ion m/z, the consensus RI, the consensus MS1 sample component, and the consensus MS2 sample component of the candidate component clusters with an unknown compound in the samples.

2. The method of claim 1, wherein removing any MS2 sample component from the data set corresponding to one of the known compounds comprises removing any of a known molecular ion, a background artifact, a chromatographic artifact, or a derivative relationship of the known molecular ion, a mass relationship of the known molecular ion, the background artifact, or the chromatographic artifact, corresponding to one of the known compounds, from the data set.

3. The method of claim 2, wherein removing the derivative relationship of the known molecular ion or the mass relationship of the known molecular ion from the data set comprises removing any of an in-source fragment, an adduct, an isotope, a dimer, an oligomer, a multiple charged species, an adduct of an isotope, or an oligomer of an isotope, from the data set.

4. The method of claim 1, comprising determining precursor ion mass-to-charge ratios and retention indices of the known compounds from the MS1 sample components thereof.

5. The method of claim 4, comprising associating any of the precursor ion m/z, the RI, the MS1 sample components, and the MS2 sample components of each known compound with the respective known compound in a database comprising an ion data repository.

6. The method of claim 1, comprising associating the precursor ion m/z, the RI, MS1 sample components, and the MS2 sample components of each candidate component cluster with the unknown compound in a database comprising an ion data repository.

7. The method of claim 1, comprising determining the retention index by normalizing a retention time for each MS2 sample component.

8. The method of claim 1, wherein forming component clusters across the candidate MS2 sample components comprises forming component clusters across the candidate MS2 sample components using divisive clustering or agglomerative clustering.

9. The method of claim 1, comprising sorting the candidate MS2 sample components by precursor ion mass prior to forming the component clusters across the candidate MS2 sample components.

10. The method of claim 9, comprising sorting the component clusters by retention index to generate secondary component clusters.

11. The method of claim 1, wherein the step of forming component clusters across the candidate MS2 sample components is repeated two or more times.

12. The method of claim 1, wherein comparing the consensus MS1 sample component for each component cluster, across the component clusters, is performed across a plurality of the samples.

13. The method of claim 12, comprising removing any component clusters that are present in less than 5% of the plurality of samples.

14. The method of claim 1, comprising analyzing a plurality of possible derivative relationships or possible mass relationships of the MS1 sample components prior to associating the consensus MS1 sample component with a corresponding consensus precursor ion m/z.

15. The method of claim 14, wherein analyzing the plurality of possible derivative relationships or the plurality of possible mass relationships comprises analyzing the plurality of possible derivative relationships or possible mass relationships using symbolic algebra in a single run to generate computer code for analyzing a set of specified derivative relationships or mass relationships.

16. The method of claim 1, comprising removing any component clusters lacking a plausible molecular formula, prior to grouping the component clusters.

17. The method of claim 1, comprising removing any component clusters lacking statistical significance from metadata of the data of the one or more samples being analyzed, prior to grouping the component clusters.

18. The method of claim 1, comprising prioritizing candidate component clusters having statistical significance with respect to metadata of the data of the one or more samples being analyzed as candidate unknown compounds.

19. An apparatus for analyzing data for one or more samples, the data for each sample being obtained from a component separation and tandem mass spectrometer system comprising a separation portion, including a liquid chromatograph, a gas chromatograph, a supercritical fluid chromatograph, or a capillary electrophoresis analyzer, and a first mass spectrometry step or provision (MS1) and a second mass spectrometry step or provision (MS2), the apparatus comprising a processor and a memory storing executable instructions that, in response to execution by the processor, cause the apparatus to at least:

analyze, for each sample, a data set for a plurality of MS2 sample components to determine a precursor ion mass-to-charge ratio (m/z) and a retention index (RI) for each MS2 sample component;

compare the precursor ion m/z and the RI for each MS2 sample component to precursor ion mass-to-charge ratios and retention indices of known compounds and remove any MS2 sample component from the data set corresponding to one of the known compounds, with remaining MS2 sample components in the data set being candidate MS2 sample components;

form component clusters across the candidate MS2 sample components, each component cluster including candidate MS2 sample components each having the precursor ion m/z and the RI within respective ranges for the component cluster;

for each sample within each component cluster, retrieve one or more MS1 sample components within the respective precursor ion m/z and RI ranges for the component cluster;

for each component cluster, determine at most one consensus MS1 sample component, by aggregating the one or more MS1 sample components within the respective precursor ion m/z and RI ranges, to represent each sample, and associate the consensus MS1 sample component with a corresponding consensus MS2 sample component, consensus precursor ion m/z, and consensus RI determined by aggregating the MS2 sample components and associated precursor ion m/z and the RI within the component cluster;

for each component cluster, determine whether the consensus MS1 sample component indicates a molecular ion or a derivative relationship to the molecular ion;

group component clusters according to consensus RI and select one or more component clusters from each group of component clusters, the one or more component clusters being candidate component clusters; and correlate the consensus precursor ion m/z, the consensus RI, the consensus MS1 sample component, and the consensus MS2 sample component of the candidate component clusters with an unknown compound in the samples.

20. The apparatus of claim 19, wherein the processor executing the executable instructions causing the apparatus to at least remove any MS2 sample component from the data set corresponding to one of the known compounds further comprises causing the apparatus to remove any of a known molecular ion, a background artifact, a chromatographic artifact, or a derivative relationship of the known molecular ion, a mass relationship of the known molecular ion, the background artifact, or the chromatographic artifact, corresponding to one of the known compounds, from the data set.

21. The apparatus of claim 20, wherein the processor executing the executable instructions causing the apparatus to at least remove the derivative relationship of the known molecular ion or the mass relationship of the known molecular ion from the data set further comprises causing the apparatus to remove any of an in-source fragment, an adduct, an isotope, a dimer, an oligomer, a multiple charged species, an adduct of an isotope, or an oligomer of an isotope, from the data set.

22. The apparatus of claim 19, wherein the processor executing the executable instructions further causes the apparatus to at least determine precursor ion mass-to-charge ratios and retention indices of the known compounds from the MS1 sample components thereof.

23. The apparatus of claim 22, wherein the processor executing the executable instructions further causes the apparatus to at least associate any of the precursor ion m/z, the RI, the MS1 sample components, and the MS2 sample components of each known compound with the respective known compound in a database comprising an ion data repository.

24. The apparatus of claim 19, wherein the processor executing the executable instructions further causes the apparatus to at least associate the precursor ion m/z, the RI, MS1 sample components, and the MS2 sample components of each candidate component cluster with the unknown compound in a database comprising an ion data repository.

25. The apparatus of claim 19, wherein the processor executing the executable instructions further causes the apparatus to at least determine the retention index by normalizing a retention time for each MS2 sample component.

26. The apparatus of claim 19, wherein the processor executing the executable instructions causing the apparatus to at least form component clusters across the candidate MS2 sample components further comprises causing the apparatus to form component clusters across the candidate MS2 sample components using divisive clustering or agglomerative clustering.

27. The apparatus of claim 19, wherein the processor executing the executable instructions further causes the apparatus to at least sort the candidate MS2 sample components by precursor ion mass prior to forming the component clusters across the candidate MS2 sample components.

28. The apparatus of claim 27, wherein the processor executing the executable instructions further causes the apparatus to at least sort the component clusters by retention index to generate secondary component clusters.

29. The apparatus of claim 19, wherein the processor executing the executable instructions further causes the apparatus to at least repeat the step of forming component clusters across the candidate MS2 sample components two or more times.

30. The apparatus of claim 19, wherein the processor executing the executable instructions further causes the apparatus to compare the consensus MS1 sample component for each component cluster, across the component clusters, and across a plurality of the samples.

31. The apparatus of claim 30, wherein the processor executing the executable instructions further causes the apparatus to remove any component clusters that are present in less than 5% of the plurality of samples.

32. The apparatus of claim 19, wherein the processor executing the executable instructions further causes the apparatus to analyze a plurality of possible derivative relationships or possible mass relationships of the MS1 sample components prior to associating the consensus MS1 sample component with a corresponding consensus precursor ion m/z.

33. The apparatus of claim 32, wherein the processor executing the executable instructions causing the apparatus to analyze the plurality of possible derivative relationships or the plurality of possible mass relationships further comprises causing the apparatus to analyze the plurality of possible derivative relationships or possible mass relationships using symbolic algebra in a single run to generate computer code for analyzing a set of specified derivative relationships or mass relationships.

34. The apparatus of claim 19, wherein the processor executing the executable instructions further causes the apparatus to remove any component clusters lacking a plausible molecular formula, prior to grouping the component clusters.

35. The apparatus of claim 19, wherein the processor executing the executable instructions further causes the apparatus to remove any component clusters lacking statistical significance from metadata of the data of the one or more samples being analyzed, prior to grouping the component clusters.

36. The apparatus of claim 19, wherein the processor executing the executable instructions further causes the apparatus to prioritize candidate component clusters having statistical significance with respect to metadata of the data of the one or more samples being analyzed as candidate unknown compounds.

37. A computer program product for analyzing data for one or more samples, the data for each sample being obtained from a component separation and tandem mass spectrometer system comprising a separation portion, including a liquid chromatograph, a gas chromatograph, a supercritical fluid chromatograph, or a capillary electrophoresis analyzer, and a first mass spectrometry step (MS1) and a second mass spectrometry step (MS2), the computer program product comprising at least one non-transitory computer readable storage medium having computer-readable program code stored thereon, the computer-readable program code comprising program code for performing at least the method steps of:

analyzing, for each sample, a data set for a plurality of MS2 sample components to determine a precursor ion mass-to-charge ratio (m/z) and a retention index (RI) for each MS2 sample component;

comparing the precursor ion m/z and the RI for each MS2 sample component to precursor ion mass-to-charge ratios and retention indices of known compounds and removing any MS2 sample component from the data set corresponding to one of the known compounds, with remaining MS2 sample components in the data set being candidate MS2 sample components;

forming component clusters across the candidate MS2 sample components, each component cluster including candidate MS2 sample components each having the precursor ion m/z and the RI within respective ranges for the component cluster;

for each sample within each component cluster, retrieving one or more MS1 sample components within the respective precursor ion m/z and RI ranges for the component cluster;

for each component cluster, determining at most one consensus MS1 sample component, by aggregating the one or more MS1 sample components within the respective precursor ion m/z and RI ranges, to represent each sample, and associating the consensus MS1 sample component with a corresponding consensus MS2 sample component, consensus precursor ion m/z, and consensus RI determined by aggregating the MS2 sample components and associated precursor ion m/z and the RI within the component cluster;

for each component cluster, determining whether the consensus MS1 sample component indicates a molecular ion or a derivative relationship to the molecular ion;

grouping component clusters according to consensus RI and selecting one or more component clusters from each group of component clusters, the one or more component clusters being candidate component clusters; and correlating the consensus precursor ion m/z, the consensus RI, the consensus MS1 sample component, and the consensus MS2 sample component of the candidate component clusters with an unknown compound in the samples.

38. The computer program product of claim 37, wherein the program code for removing any MS2 sample component from the data set corresponding to one of the known compounds further comprises program code for removing any of a known molecular ion, a background artifact, a chromatographic artifact, or a derivative relationship of the known molecular ion, a mass relationship of the known molecular ion, the background artifact, or the chromatographic artifact, corresponding to one of the known compounds, from the data set.

39. The computer program product of claim 38, wherein the program code for removing the derivative relationship of the known molecular ion or the mass relationship of the known molecular ion from the data set further comprises program code for removing any of an in-source fragment, an adduct, an isotope, a dimer, an oligomer, a multiple charged species, an adduct of an isotope, or an oligomer of an isotope, from the data set.

40. The computer program product of claim 37, wherein the computer-readable program code further comprises program code for determining precursor ion mass-to-charge ratios and retention indices of the known compounds from the MS1 sample components thereof.

41. The computer program product of claim 40, wherein the computer-readable program code further comprises program code for associating any of the precursor ion m/z, the RI, the MS1 sample components, and the MS2 sample components of each known compound with the respective known compound in a database comprising an ion data repository.

42. The computer program product of claim 37, wherein the computer-readable program code further comprises program code for associating the precursor ion m/z, the RI, MS1 sample components, and the MS2 sample components of each candidate component cluster with the unknown compound in a database comprising an ion data repository.

43. The computer program product of claim 37, wherein the computer-readable program code further comprises program code for determining the retention index by normalizing a retention time for each MS2 sample component.

44. The computer program product of claim 37, wherein the program code for forming component clusters across the candidate MS2 sample components further comprises program code for forming component clusters across the candidate MS2 sample components using divisive clustering or agglomerative clustering.

45. The computer program product of claim 37, wherein the computer-readable program code further comprises program code for sorting the candidate MS2 sample components by precursor ion mass prior to forming the component clusters across the candidate MS2 sample components.

46. The computer program product of claim 45, wherein the computer-readable program code further comprises program code for sorting the component clusters by retention index to generate secondary component clusters.

47. The computer program product of claim 37, wherein the computer-readable program code further comprises program code for repeating the step of forming component clusters across the candidate MS2 sample components two or more times.

48. The computer program product of claim 37, wherein the computer-readable program code further comprises program code for comparing the consensus MS1 sample component for each component cluster, across the component clusters, and across a plurality of the samples.

49. The computer program product of claim 48, wherein the computer-readable program code further comprises program code for removing any component clusters that are present in less than 5% of the plurality of samples.

50. The computer program product of claim 37, wherein the computer-readable program code further comprises program code for analyzing a plurality of possible derivative relationships or possible mass relationships of the MS1 sample components prior to associating the consensus MS1 sample component with a corresponding consensus precursor ion m/z.

51. The computer program product of claim 50, wherein the program code for analyzing the plurality of possible derivative relationships or the plurality of possible mass relationships further comprises program code for analyzing the plurality of possible derivative relationships or possible mass relationships using symbolic algebra in a single run to generate computer code for analyzing a set of specified derivative relationships or mass relationships.

52. The computer program product of claim 37, wherein the computer-readable program code further comprises program code for removing any component clusters lacking a plausible molecular formula, prior to grouping the component clusters.

53. The computer program product of claim 37, wherein the computer-readable program code further comprises program code for removing any component clusters lacking statistical significance from metadata of the data of the one or more samples being analyzed, prior to grouping the component clusters.

54. The computer program product of claim 37, wherein the computer-readable program code further comprises program code for prioritizing candidate component clusters having statistical significance with respect to metadata of the data of the one or more samples being analyzed as candidate unknown compounds.

* * * * *